(12) United States Patent
Levine et al.

(10) Patent No.: US 8,502,963 B2
(45) Date of Patent: *Aug. 6, 2013

(54) METHOD AND APPARATUS FOR ANALYZING INDIVIDUAL CELLS OR PARTICULATES USING FLUORESCENT QUENCHING AND/OR BLEACHING

(71) Applicants: Robert A. Levine, Guilford, CT (US); Stephen C. Wardlaw, Lyme, CT (US); Niten V. Lalpuria, Mumbai (IN); Darryn W. Unfricht, North Haven, CT (US)

(72) Inventors: Robert A. Levine, Guilford, CT (US); Stephen C. Wardlaw, Lyme, CT (US); Niten V. Lalpuria, Mumbai (IN); Darryn W. Unfricht, North Haven, CT (US)

(73) Assignee: Abbott Point of Care, Inc., Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/645,075

(22) Filed: Oct. 4, 2012

(65) Prior Publication Data

US 2013/0029373 A1 Jan. 31, 2013

Related U.S. Application Data

(60) Continuation of application No. 13/330,236, filed on Dec. 19, 2011, now Pat. No. 8,284,384, which is a division of application No. 12/408,448, filed on Mar. 20, 2009, now Pat. No. 8,081,303.

(60) Provisional application No. 61/038,578, filed on Mar. 21, 2008.

(51) Int. Cl.
*G01N 33/48* (2006.01)

(52) U.S. Cl.
CPC .................................... *G01N 33/48* (2013.01)
USPC ............................................. 356/39; 356/40

(58) Field of Classification Search
CPC ...................................................... G01N 33/48
USPC ...................................................... 356/39–42
See application file for complete search history.

(56) References Cited

U.S. PATENT DOCUMENTS

| 4,023,716 A | 5/1977 | Shapiro |
| 4,197,088 A | 4/1980 | Meserol et al. |

(Continued)

FOREIGN PATENT DOCUMENTS

| DE | 10011235 | 9/2001 |
| DE | 10240742 | 3/2004 |

(Continued)

OTHER PUBLICATIONS

Sun et al, "Microminiaturized immunoassays using quantum dots as fluorescent label by laser confocal scanning fluorescence detection," Journal of Immunological Methods, Elsevier Science Publishers, vol. 249, No. 1-2, pp. 85-89, Mar. 2001.

(Continued)

*Primary Examiner* — Michael P Stafira
(74) *Attorney, Agent, or Firm* — O'Shea Getz P.C.

(57) ABSTRACT

A method for analyzing a blood sample is provided that includes the steps of: providing a blood sample having one or more of each first and second constituents; admixing a colorant with the sample, which colorant is operative to cause the first constituents and second constituents to fluoresce and absorb light; illuminating at least a portion of the sample; e) imaging a portion of the sample; determining a fluorescence value for each the first constituents and second constituents; determining an optical density value for each of the first constituents and second constituents; and identifying the first constituents and the second constituents using the determined fluorescence and optical density values.

20 Claims, 6 Drawing Sheets

U.S. PATENT DOCUMENTS

| | | | |
|---|---|---|---|
| 4,487,081 | A | 12/1984 | De Vaughn et al. |
| 4,500,509 | A | 2/1985 | Kass |
| 4,615,878 | A | 10/1986 | Kass |
| 4,963,498 | A * | 10/1990 | Hillman et al. ............ 436/69 |
| 5,012,818 | A | 5/1991 | Joishy |
| 5,068,181 | A | 11/1991 | Driscoll |
| 5,192,511 | A | 3/1993 | Roach |
| 5,284,771 | A | 2/1994 | Fan et al. |
| 5,300,779 | A * | 4/1994 | Hillman et al. ............ 250/341.1 |
| 5,447,838 | A | 9/1995 | Meiklejohn et al. |
| 5,454,268 | A | 10/1995 | Kim |
| 5,460,782 | A | 10/1995 | Coleman et al. |
| 5,739,042 | A | 4/1998 | Frengen |
| 5,768,407 | A | 6/1998 | Shen et al. |
| 5,770,160 | A | 6/1998 | Smith et al. |
| 6,004,821 | A | 12/1999 | Levine et al. |
| 6,127,184 | A | 10/2000 | Wardlaw |
| 6,235,536 | B1 | 5/2001 | Wardlaw |
| 6,448,088 | B1 | 9/2002 | Levine et al. |
| 6,723,290 | B1 | 4/2004 | Wardlaw |
| 6,730,521 | B1 | 5/2004 | Cassells |
| 6,866,823 | B2 | 3/2005 | Wardlaw |
| 6,869,570 | B2 | 3/2005 | Wardlaw |
| 6,929,953 | B1 | 8/2005 | Wardlaw |
| 7,634,125 | B2 | 12/2009 | Ortyn et al. |
| 7,903,241 | B2 | 3/2011 | Wardlaw |
| 7,929,121 | B2 | 4/2011 | Wardlaw et al. |
| 7,929,122 | B2 | 4/2011 | Wardlaw et al. |
| 8,077,296 | B2 | 12/2011 | Levine et al. |
| 8,081,303 | B2 | 12/2011 | Levine et al. |
| 2001/0030741 | A1 * | 10/2001 | Herron et al. ............ 356/39 |
| 2002/0028158 | A1 | 3/2002 | Wardlaw |
| 2002/0131902 | A1 | 9/2002 | Levy |
| 2003/0025896 | A1 | 2/2003 | Oever et al. |
| 2003/0165960 | A1 * | 9/2003 | Kopf-Sill et al. ............ 435/6 |
| 2003/0224534 | A1 | 12/2003 | Kawate |
| 2004/0048330 | A1 | 3/2004 | Bittner |
| 2004/0165090 | A1 | 8/2004 | Ning |
| 2005/0002826 | A1 | 1/2005 | Oguni et al. |
| 2005/0026197 | A1 | 2/2005 | Dertinger |
| 2005/0277159 | A1 | 12/2005 | Lehmann et al. |
| 2006/0159962 | A1 | 7/2006 | Chandler et al. |
| 2006/0258018 | A1 | 11/2006 | Curl et al. |
| 2007/0087442 | A1 | 4/2007 | Wardlaw |
| 2007/0243117 | A1 | 10/2007 | Wardlaw |
| 2008/0070317 | A1 | 3/2008 | Bradshaw et al. |

FOREIGN PATENT DOCUMENTS

| | | | |
|---|---|---|---|
| EP | 0366151 | 5/1990 | ............ 33/543 |
| EP | 0642829 | 3/1995 | |
| EP | 1239284 | 9/2002 | ............ 33/53 |
| GB | 2254414 | 10/1992 | ............ 21/84 |
| WO | WO 9802727 | 1/1998 | ............ 15/14 |
| WO | WO 0057891 | 5/2000 | |
| WO | WO 0223154 | 3/2002 | ............ 33/558 |

OTHER PUBLICATIONS

Goldman et al., "Multiplexed Toxin Analysis using Four Colors of Quantum Dot Fluororeagents," Analytical Chemistry, American Chemical Society, vol. 76, No. 3, pp. 684-688, Feb. 2004.

Matzdorff et al., "Quantitative assessment of platelets, platelet microparticles, and platelet aggregates in flow cytometry," The Journal of Laboratory and Clinical Medicine, vol. 131, No. 6, pp. 507-517, Jun. 1998.

Hu Hu et al, "Effects of insulin on platelet and leukocyte activity in whole blood," Thrombosis Research, vol. 107, No. 5, pp. 209-215, Sep. 2002.

Sbrana et al., "Relationships between optica aggregometry (type born) and flow cytometry in evaluating ADP-induced platelet activation," Cytometry, Part B, Clinical Cytometry, vol. 74, No. 1, pp. 30-39, Jan. 2008.

* cited by examiner

METHOD AND APPARATUS FOR ANALYZING INDIVIDUAL CELLS OR PARTICULATES USING FLUORESCENT QUENCHING AND/OR BLEACHING

The present application is a continuation of U.S. patent application Ser. No. 13/330,236 filed Dec. 19, 2011, which is a divisional of U.S. Pat. No. 8,081,303 filed Dec. 20, 2011, which is entitled to the benefit of and incorporates by reference essential subject matter disclosed in U.S. Provisional Patent Application Ser. No. 61/038,578, filed Mar. 21, 2008.

BACKGROUND OF THE INVENTION

1. Technical Field

The present invention relates to apparatus and methods for analysis of blood samples in general, and apparatus and methods for detecting, identifying, and enumerating constituents, such as cells or particulates, within the sample in particular.

2. Background Information

Physicians, veterinarians and scientists have examined human and animals' biologic fluids, especially blood, in order to determine constituent quantities as well as to identify the presence of unusual constituents not seen in healthy subjects. The constituents generally measured, quantified and identified include red blood cells (RBCs), white blood cells (WBCs), and platelets. RBC analyses can include determinations of RBC number, size, volume, shape, hemoglobin content and concentration, and the hematocrit (also referred to as the packed cell volume). RBC analyses can also involve determining the presence and/or concentration of certain components within the red cells such as DNA, RNA, including the detection of the presence and/or enumeration of hematoparasites (e.g., malarial parasites) either in the RBCs or trypanosomes which are extracellular or leishmaniasis organisms which are in the WBCs as well as many other hematoparasites. WBC analyses can include a determination of the population frequency of WBC sub-types generally referred to as a differential WBC count, as well as the notification of any unusual cell types not found in healthy subjects. Platelet (or in certain animals including birds, reptiles and fish, thrombocytes which are similar in function to platelets in mammals but are about ten times larger and nucleated) analyses can include platelet number, size, shape texture, and volume determinations, including determining the presence of clumps of platelets or thrombocytes within the sample.

Known blood examination techniques, described in detail medical texts such as Wintrobe's Clinical Hematology 12$^{th}$ Edition, generally divides the examination methods into manual, centrifugal, and impedance type methods. Manual methods typically involve the creation of an accurately determined volume of a blood or fluid sample that is quantitatively diluted and visually counted in a counting chamber. Manual examination methods include examining a peripheral smear where the relative amounts of the particulate types are determined by visual inspection. Centrifugal examination methods involve centrifuging the sample, causing the sample to separate into constituent layers according to the relative densities of the constituents. The component layers can be stained to enhance visibility or detection. Impedance methods involve the examination of an accurate volume of blood which is treated according to the particulate being measured; e.g., lysing RBCs for enumeration of the nucleated cells and volumetrically diluting the sample in a conductive fluid. The process typically involves monitoring a current or voltage applied to sample passing through a narrow passage to determine the effect particles have on the current/voltage as the particles pass through in single file. Other techniques involve analyzing the intensity and angle of scatter of light incident to particulates passing single file through a light beam. Flow cytometric methods can also be used that involve staining particulates of interest in suspension with fluorophores attached to antibodies directed against surface epitopes present on cell or particle types, exciting the stained particulates with light of appropriate wavelengths, and analyzing the emission of the individual particulates/cells.

All of the aforementioned methods, other than the peripheral smear or centrifugal separation, require dispensing a precise volume of sample. Inaccuracies in the sample volume will result in quantitative errors of the same magnitude in the associated analysis. With the exception of centrifugal methods, all of the aforementioned methods also require the sample to be mixed with one or more liquid reagents or diluents, and also require calibration of the instrument to obtain accurate results. In the case of peripheral smears, a high degree of training is needed to properly examine the smear. A number of the aforementioned methods generate large volumes of contaminated waste which is expensive to handle. Additionally, the above-described methods are not suitable to determine the complete blood count (CBC) in birds, reptiles, fish where the red blood cells and thrombocytes are nucleated and in certain mammals where the red blood cells size is very small and may be confused with platelets.

The amount of information that can be determined by examining the blood of a human or animal is vast. It is particularly useful to determine the indices of RBCs; e.g., individual cell size, individual cell hemoglobin content and concentration, and population statistics of RBCs within a sample. The mean and dispersion statistics (e.g., coefficients of variation) for each of the aforementioned parameters can also provide important information, as is evidenced by their discussion within the above-referenced text by Wintrobe, which has enabled physicians to better categorize disorders of RBCs.

SUMMARY OF THE INVENTION

A method and apparatus is provided for analyzing constituents within a quiescent blood sample. According to one aspect of the invention, a method for analyzing a blood sample is provided that includes the steps of: a) providing a substantially undiluted blood sample having one or more first constituents and one or more second constituents, which second constituents are different from the first constituents; b) depositing the sample into an analysis chamber adapted to quiescently hold the sample for analysis, the chamber defined by a first panel and a second panel, both of which panels are transparent; c) admixing a colorant with the sample, which colorant is operative to cause the first constituents and second constituents to fluoresce upon exposure to predetermined first wavelengths of light, and which colorant is operative to absorb light at one or more predetermined second wavelengths of light; d) illuminating at least a portion of the sample containing the first constituents and the second constituents at the first wavelengths and at the second wavelengths; e) imaging the at least a portion of the sample, including producing image signals indicative of fluorescent emissions from the first constituents and the second constituents and the optical density of the first constituents and the second constituents; f) determining a fluorescence value for each of the first constituents and second constituents using the image signals; g) determining an optical density value for each of the first constituents and second constituents, which optical density is a function of the colorant absorbed by the constituents, using the image signals; and h) identifying the first constituents and the second constituents using the determined fluorescence and optical density values.

According to another aspect of the present invention, a method for analyzing a blood sample is provided that includes the steps of: a) providing a substantially undiluted blood sample having one or more first particulates and one or more second particulates, which second particulates are different from the first particulates; b) depositing the sample into an analysis chamber adapted to quiescently hold the sample for analysis, the chamber defined by a first panel and a second panel, both of which panels are transparent; c) admixing a colorant with the sample, which colorant is operative to cause the first particulates and second particulates to fluoresce upon exposure to predetermined first wavelengths of light, and which colorant is operative to absorb light at one or more predetermined second wavelengths of light; d) illuminating at least a portion of the sample containing the first particulates and the second particulates at the first wavelengths and at the second wavelengths; e) imaging the at least a portion of the sample, including producing image signals indicative of fluorescent emissions from the first particulates and the second particulates and the optical density of the first particulates and the second particulates; f) determining one or more fluorescent emission values for each the first particulates and second particulates using the image signals; g) determining one or more optical density values for each of the first particulates and second particulates, which optical density is a function of the colorant absorbed by the particulates, using the image signals; and h) identifying the first particulates and the second particulates using the determined fluorescent emission and optical density values.

According to a still further aspect of the present invention, a method for analyzing a blood sample is provided that includes the steps of: a) providing a substantially undiluted blood sample having one or more first constituents and one or more second constituents, which second constituents are different from the first constituents; b) depositing the sample into an analysis chamber adapted to quiescently hold the sample for analysis, the chamber defined by a first panel and a second panel, both of which panels are transparent; c) admixing a colorant with the sample, which colorant is operative to cause the first constituents and second constituents to fluoresce upon exposure to predetermined wavelengths of light; d) illuminating at least a portion of the sample containing the first constituents and the second constituents at the wavelengths of light in a constant manner for a period of time; e) imaging the at least a portion of the sample at discrete points in time during the period, and producing image signals indicative of fluorescent emissions from the first constituents and the second constituents for each discrete point in time; f) determining one or more fluorescent emission values for each of the first constituents and second constituents quiescently disposed within the sample using the image signals for each discrete point in time, and a rate of change for the fluorescent emission values between the discrete point in time for each of the first and second constituents; and g) identifying the first constituents and the second constituents using the determined rate of change of the fluorescent emission values for each of the first and second constituents.

An advantage of the present invention is that it can be used to determine characteristics of a blood sample using an extremely small sample volume that may be obtained directly from the patient by capillary puncture rendering it more useful for point of care application or from a venous sample if desired.

Another advantage of the present method is that it operates free of external and internal fluidics, and independent of gravity or orientation, and therefore is adaptable for use in a hand held device and in microgravity conditions.

The present method and advantages associated therewith will become more readily apparent in view of the detailed description provided below, including the accompanying drawings.

DETAILED DESCRIPTION OF EMBODIMENTS OF THE INVENTION

The present method utilizes an analysis chamber that is operable to quiescently hold a sample of substantially undiluted anticoagulated whole blood for analysis. The chamber is typically sized to hold about 0.2 to 1.0 µl of sample, but the chamber is not limited to any particular volume capacity, and the capacity can vary to suit the analysis application. The phrase "substantially undiluted" as used herein describes a blood sample which is either not diluted at all or has not been diluted purposefully, but has had some reagents added thereto for purposes of the analysis. To the extent the addition of the reagents dilutes the sample, if at all, such dilution has no clinically significant impact on the analysis performed. Typically, the only reagents that will be used in performing the present method are anticoagulants (e.g., EDTA, heparin) and colorants. These reagents are generally added in dried form and are not intended to dilute the sample. Under certain circumstances (e.g., very rapid analysis), it may not be necessary to add an anticoagulating agent, but it is preferable to do so in most cases to ensure the sample is in a form acceptable for analysis. The term "quiescent" is used to describe that the sample is deposited within the chamber for analysis, and the sample is not purposefully moved relative to the chamber during the analysis; i.e., the sample resides quiescently within the chamber. To the extent that motion is present within the blood sample, it will predominantly be that due to Brownian motion of the blood sample's formed constituents, which motion is not disabling of the use of the device of this invention.

The colorant (e.g., a dye, stain, etc.), which is admixed with at least a portion of the blood sample, facilitates quantitative analysis of the constituents (e.g., WBCs and other nuclear containing cells, and particulates including platelets, and other constituents containing DNA and/or RNA—e.g., intracellular or extracellular hematoparasites—etc.) that absorb the colorant. The cells and particulates may be collectively referred to herein as "constituents" within the sample. The colorant fluoresces along characteristic wavelengths (e.g., 530 nm, 585 nm, and 660 nm) when excited by light along certain wavelengths (e.g., about 470 nm). The specific wavelengths at which a cell will fluoresce are a characteristic of that cell and the wavelength(s) of the exciting light. The colorant also absorbs light at one or more predetermined wavelengths as a function of the concentration of the colorant within the cell. Examples of acceptable colorants include the supravital dyes acridine orange and astrozone orange. The invention is not limited to supravital dyes, however.

Figure 1:
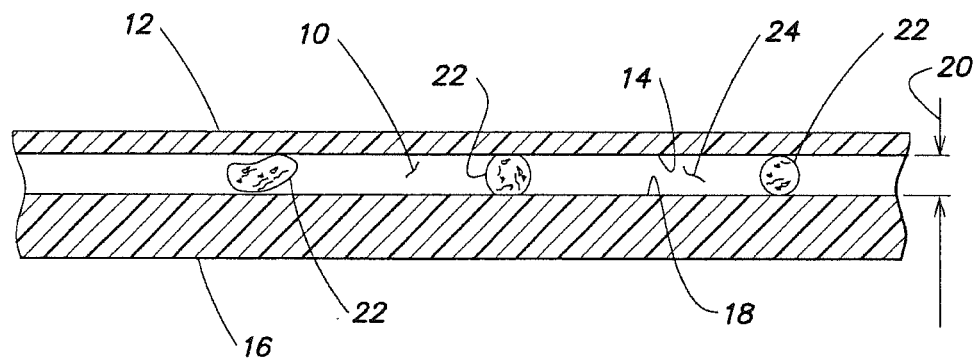
FIGS. 1-4 are cross-sectional diagrammatic representations of analysis chambers that may be used in the present method.
Figure 2:
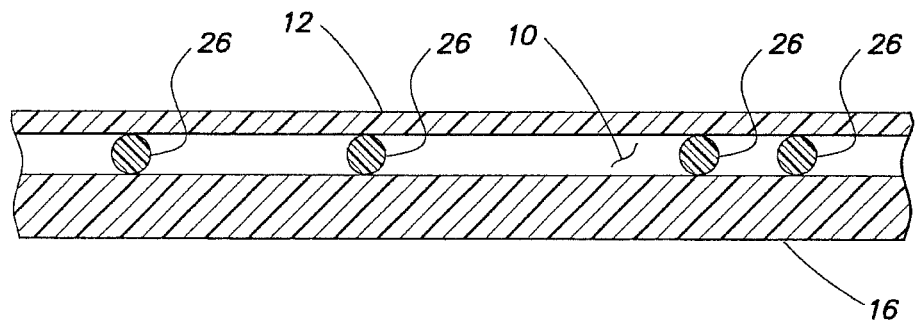

Now referring to FIG. 1, the analysis chamber 10 is defined by a first panel 12 having an interior surface 14, and a second panel 16 having an interior surface 18. The panels 12, 16 are both sufficiently transparent to allow the transmission of light along predetermined wavelengths there through in an amount sufficient to perform the optical density analysis described below. At least a portion of the panels 12, 16 are parallel with one another, and within that portion the interior surfaces 14, 18 are separated from one another by a height 20, which height may be known or measurable. RBCs 22 are shown disposed within the chamber 10.

The present method can utilize a variety of different analysis chambers types having the aforesaid characteristics, and is not therefore limited to any particular type of analysis chamber. An analysis chamber having parallel panels 12, 16 simplifies the analysis and is therefore preferred, but is not required for the present invention; e.g., a chamber having one panel disposed at a known non-parallel angle relative to the other panel could be used.

Now referring to FIGS. 2-5, an example of an acceptable chamber 10 is shown that includes a first panel 12, a second panel 16, and at least three separators 26 disposed between the panels 12, 15. The separators 26 can be any structure that is disposable between the panels 12, 16, operable to space the panels 12, 16 apart from one another. The dimension 28 of a separator 26 that extends between the panels 12, 16 is referred to herein as the height 28 of the separator 26. The heights 28 of the separators 26 typically do not equal one another exactly (e.g., manufacturing tolerances), but are within commercially acceptable tolerance for spacing means used in similar analysis apparatus. Spherical beads are an example of an acceptable separator 26 and are commercially available from, for example, Bangs Laboratories of Fishers, Indiana, U.S.A.

Figure 3:
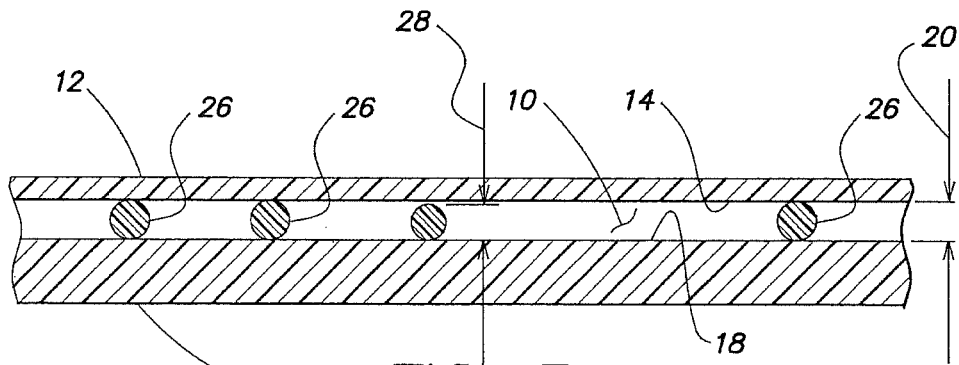
Figure 4:
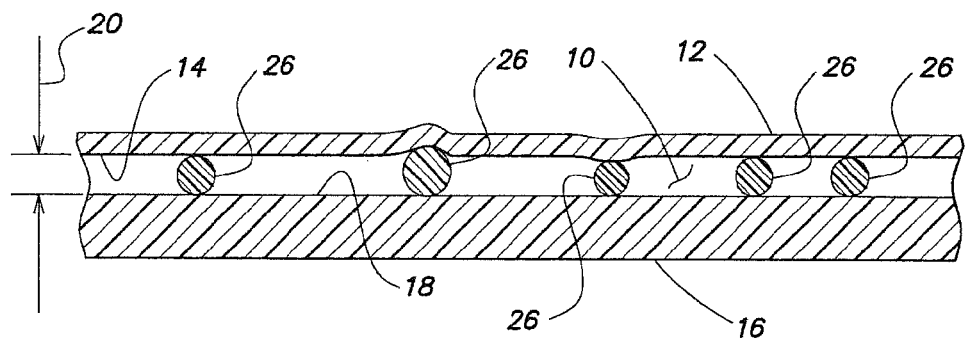
Figure 5:
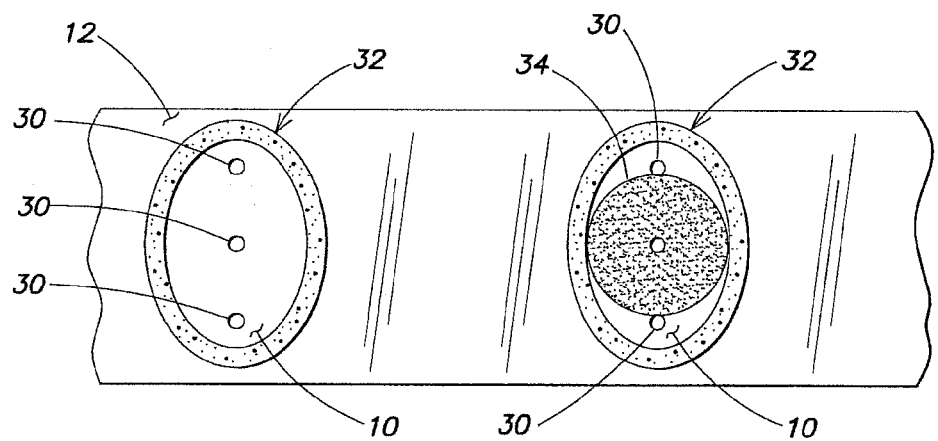
FIG. 5 is a diagrammatic planar view of a tape having a plurality of analysis chambers.

In the chamber embodiment shown in FIG. 3, the separators 26 consist of a material that has greater flexibility than one or both of the first panel 12 and the second panel 16. As can be seen in FIG. 3, the larger separators 26 are compressed to the point where most separators 26 are touching the interior surfaces of the panels 12, 16, thereby making the chamber height just slightly less than the mean separator 26 diameters. In the chamber embodiment shown in FIG. 4, the separators 26 consist of a material that has less flexibility than one or both of the first panel 12 and the second panel 16. In FIG. 4, the first panel 12 is formed from a material more flexible than the spherical separators 26 and the second panel 16, and will overlay the separators 26 in a tent-like fashion. In this embodiment, although small local regions of the chamber 10 may deviate from the desired chamber height 20, the average height 20 of the chamber 10 will be very close to that of the mean separator 26 diameter. Analysis indicates that the mean chamber height 20 can be controlled to about one percent (1%) or better at chamber heights of less than four microns using this embodiment. Subject to the flexibility characteristics described above (as well as other factors such as the distribution density of the separators), the separators 26 and panels 12, 16 can be made from a variety of materials, provided the panels 12, 16 are sufficiently transparent. Transparent plastic films consisting of acrylic or polystyrene are examples of acceptable panels 12, 16, and spherical beads made of polystyrene, polycarbonate, silicone, and the like, are acceptable separators 26. A specific example of an acceptable separator is spheres made of polystyrene that are commercially available, for example, from Thermo Scientific of Fremont, Calif., U.S.A., catalogue no. 4204A, in four micron (4 µm) diameter. Referring to FIG. 5, the panel 12 that is to be vertically disposed above the other includes a plurality of ports 30 disposed at regular intervals (e.g., that act as air vents), and the panels 12, 16 are bonded together at points. In some embodiments, the bonding material 32 forms an outer chamber wall operable to laterally contain the sample 34 within the analysis chamber 10. This example of an acceptable analysis chamber is described in greater detail in U.S. Patent Application Publication Nos. 2007/0243117, 2007/0087442, and U.S. Provisional Patent Application Nos. 61/041,783, filed Apr. 2, 2008; and 61/110,341, filed Oct. 31, 2008, all of which are hereby incorporated by reference in their entirety.

Figure 6:
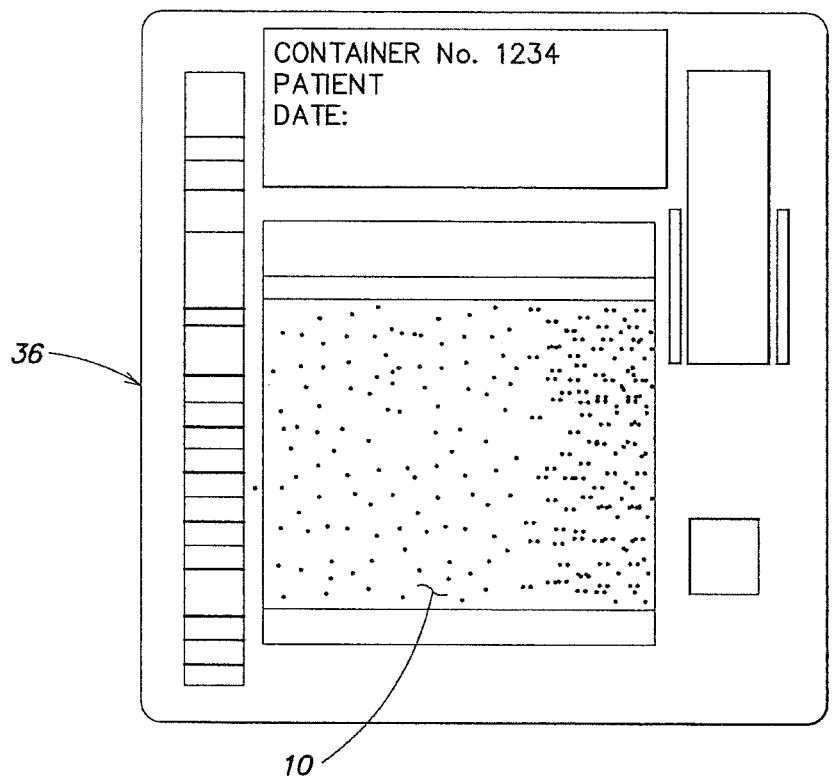
FIG. 6 is a diagrammatic planar view of a disposable container having an analysis chamber.
Figure 7:
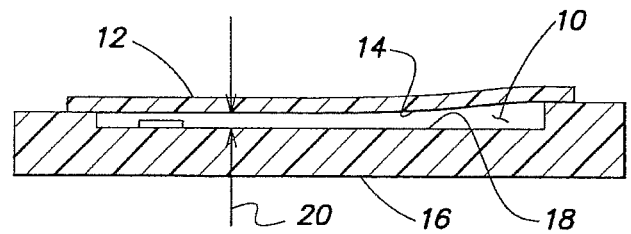
FIG. 7 is a diagrammatic cross-sectional view of a disposable container having an analysis chamber.

Another example of an acceptable chamber 10 is disposed in a disposable container 36 as shown in FIGS. 6 and 7. The chamber 10 is formed between a first panel 12 and a second panel 16. Both the first panel 12 and the second panel 16 are transparent to allow light to pass through the chamber 10. At least a portion of the first panel 12 and the second panel 16 are parallel with one another, and within that portion the interior surfaces 14, 18 are separated from one another by a height 20. This chamber 10 embodiment is described in greater detail in U.S. Pat. No. 6,723,290, which patent is hereby incorporated by reference in its entirety. The analysis chambers shown in FIGS. 2-7, represent chambers that are acceptable for use in the present method. The present method is not, however, limited to these particular embodiments.

Some of the WBCs within the sample will likely contact both interior surfaces of the chamber panels and others will not. It is not a requirement that they contact the interior surfaces, and it is not necessary to know the exact height of the chamber for purposes of the present invention. A chamber height of about two to six microns (2-6µ) is acceptable for most animal species based on typical WBC sizes and the fact that WBCs can be deformed to some degree (e.g., partially compressed between the chamber interior surfaces). A chamber height 20 of about three to five microns (3-5µ) is particularly well suited for analyzing human blood. An analysis of an animal species having WBCs substantially larger or smaller than human WBCs can be performed in a chamber respectively having a larger or smaller chamber height, respectively.

The analysis of the sample quiescently disposed within the chamber 10 is performed using an analysis device that is operable to illuminate and image at least a portion of the sample and perform an analysis on the image. The image is produced in a manner that permits fluorescent emissions from, and the optical density of, the portion of the sample to be determined on a per unit basis. The term "per unit basis" or "image unit" means a defined incremental unit of which the image of the sample can be dissected. A "pixel", which is generally defined as the smallest element of an image that can be individually processed within a particular imaging system, is an example of an image unit, and an image unit may also include a small number of pixels in a collective unit. The magnification of an imaging device can also be described in linear terms (e.g., microns per pixel at the focal plane), where the linear dimension is along a particular axis of an orthogonal grid applied to the image. The actual area of the sample captured by pixels of the sensor at the focal plane is therefore a function of the magnification factor applied by the imaging device. Hence, it is useful but not required to know the magnification of the imaging device. The volume associated with that pixel is therefore the area of the image per pixel times the chamber height. For example if the magnification was 0.5 microns per pixel, an image occupying 200 pixels would have an area of 50 square microns, and a volume of 50 square microns times the chamber height.

Figure 8:
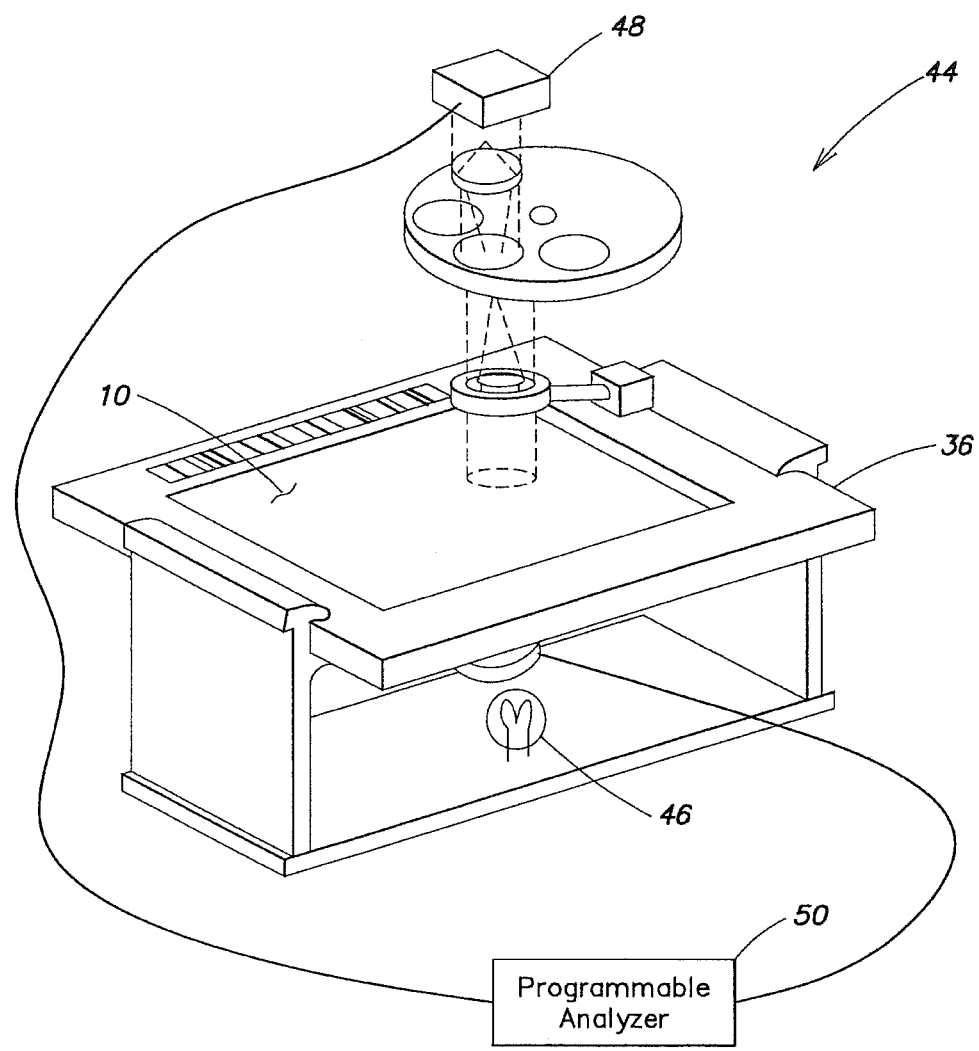
FIG. 8 is a diagrammatic schematic of an analysis device that may be used with the present method.

Now referring to FIG. 8, an example of an analysis device 44 that can be adapted for use with the present method includes a sample illuminator 46, an image dissector 48, and a programmable analyzer 50. The sample illuminator 46 includes a light source that selectively produces light along certain desired wavelengths. For example, LEDs that emit the desired wavelengths (e.g., 420 nm, 440 nm, 470 nm, etc.) can be used. Alternatively, a light source that produces a broad wavelength range (e.g., approximately 400-670 nm) can be used, although in some instances such a light source may require filtering. The analysis device 44 may include optics for manipulating the light. The sample illuminator 46 includes a transmittance light source and an epi-illumination light source, each operable to illuminate some, or all, of the sample residing within the chamber 10. An example of an acceptable image dissector 48 is a charge couple device (CCD) that converts an image of the light passing through the sample into an electronic data format (i.e., a signal). The programmable analyzer 50 includes a central processing unit (CPU) and is connected to the sample illuminator 46 and image dissector 48. The CPU is adapted (e.g., programmed) to selectively perform the functions necessary to perform the present method. U.S. Pat. No. 6,866,823 entitled "Apparatus for Analyzing Biologic Fluids" issued Mar. 15, 2005, which is hereby incorporated by reference in its entirety, discloses such an analysis device 44.

The analysis device is adapted to: 1) image at least a portion of the sample, and produce image signals indicative of fluorescent emissions from the imaged sample and the optical density of the imaged sample on a per pixel basis; 2) determine a fluorescence value for one or more constituents of a first type and one or more constituents of a second type, all quiescently residing within the sample portion, using the image signals; 3) determine an optical density value for each of the imaged first and second type constituents; and 4) identify the first type constituents and the second type constituents using the determined fluorescence and optical density values.

Under the present method, a sample of substantially undiluted whole blood is introduced into a chamber 10, and thereinafter resides quiescently as is described above. An anticoagulating agent and a colorant are admixed with the sample either prior to its introduction into the chamber or upon introduction into the chamber. The colorant is absorbed by the cells (e.g., WBCs and platelets) within the sample. Hereinafter, when referring to individual WBCs, the same procedure applies to individual platelets, or other constituents within the sample. At least a portion of the sample quiescently residing within the chamber is illuminated by the analysis device 44, which transmits light through the sample. Although it is not a requirement that the entire sample residing within the chamber be imaged, it is preferable since doing so typically provides a more complete analysis of the sample and a concomitant increase in accuracy.

The sample is illuminated with wavelengths known to excite a fluorescent emission from the cells relating to the colorant absorbed by the WBCs. WBCs stained with acridine orange produce a fluorescent emission when illuminated with violet light at a wavelength of about 470 nm The specific emissions depend upon the colorant used and the intracellular composition of the illuminated cell (e.g., interaction of the colorant with the RNA and/or DNA of the cell creates the emissions). Some WBCs have fluorescent emissions that act as a fluorometric signature that is relatively unique to that WBC and can therefore be used to identify that WBC. Other WBCs have fluorescent emission signatures that cannot easily be distinguished from one another. WBCs with those "shared" emission signatures may be grouped as being a first type WBC or a second type WBC, but something further is required to distinguish the two WBC types.

At the same time the sample is illuminated to create a fluorescent emission (or sequentially thereafter), it is also illuminated along one or more wavelengths that are absorbed by the colorant. WBCs stained with acridine orange, for example, absorb light at wavelengths of about 420 nm due to the presence of the acridine orange. The amount of absorption, which can be described in terms of optical density (OD), is a function of the concentration and local conditions (e.g., pH) of the colorant within the WBC. The propensity of a WBC to absorb a colorant, when exposed to the same amount of colorant, varies between some WBC cell types as a function of biological characteristics of the cell. For example, different biological characteristics within a WBC (e.g., nuclear material, cytoplasm, etc.) will absorb dye in different concentrations. These different biological characteristics of each cell type, and the associated different concentrations of colorant absorbed by those characteristics, can be used to distinguish certain cell types. The OD of a cell, which is a function of the concentration of a colorant within the cell, can be used to distinguish and identify different cell types. In some applications, the difference in OD between cells can provide sufficient information to permit cell identification. In other instances, identification is accomplished using the fluorometric signature and the OD of the cell.

To illustrate an example of the present invention, a substantially undiluted sample of blood is admixed with acridine orange and introduced within a chamber having two transparent panels. The sample resides quiescently and a plurality of WBCs within the sample contacts both interior surfaces of the chamber. The sample is illuminated at 470 nm and at 420 nm. The 470 nm illumination produces a fluorescent emission. The 420 nm illumination is absorbed by the colorant. Digital images of the illuminated sample are taken. A group of WBCs comprising neutrophils and eosinophils are identified within the entire WBC population present within the imaged sample, and that group is "separated" within the image; e.g., by filtering the image so that only the group can be seen. The neutrophils and the eosinophils are identified because each of these WBC types produces a signature fluorescence pattern upon excitation, consisting of a significant red cytoplasmic fluorescence and a green nuclear fluorescence. The fluorescent emissions of the neutrophils and the eosinophils within the group are, however, sufficiently similar to one another that it is difficult to distinguish the two types of WBCs.

To distinguish between the two types of WBCs within the group, the optical density of the separated WBCs are compared. On average, the concentration of the acridine orange absorbed within the eosinophils is greater than the concentration of the acridine orange absorbed within the neutrophils, although the fluorescence may be the same. This is because the fluorescence of the colorant within the eosinophils is quenched relative to that within the neutrophils because of the unique attributes of the cellular contents of the eosinophil. The two different types of WBCs can be distinguished as separate subgroups, for example, by using a predetermined OD cutoff value; e.g., those cells within the separated group having an OD greater than the cutoff value are labeled as eosinophils, and those cells having an OD that is less than the cutoff value are labeled as neutrophils.

Alternatively, the two types of WBCs can be distinguished by comparing their measured OD to empirically derived OD values stored within the analysis device; e.g., in a look up table, etc.

Still further, the two WBC subgroups can be distinguished from one another by determining the ratio of cytoplasmic fluorescence to cytoplasmic OD (fluorescence/OD) on an individual cell basis. To create the ratio, the fluorescent emission values and the optical density values on a per pixel basis for a particular cell can be determined and averaged, and the average values can be used within the ratio. The ratio can be determined using alternative methods such as determining the ratio on a per pixel basis and averaging the per pixel ratios. The ratio of fluorescence to OD quantitatively expresses the quenching of the stain's fluorescence within a particular cell. Cells having a lower ratio show "quenching" of the fluorescent signal. The ratios of all the cells within the separated group can be statistically evaluated to determine a point of separation between two populations. The cells statistically falling below the point of separation are the eosinophils because the ratio of fluorescence to OD is lower than the ratio associated with the population of neutrophils. Similarly, the cells statistically above the point of separation are the neutrophils because the ratio of fluorescence to OD is higher than the ratio of the population of eosinophils.

In a further embodiment of the above fluorescence/OD ratio analysis, the ratios can be determined using only above average OD and fluorescent emission values (or OD values and fluorescent emission values within percentage that is greater the 50%) from the cells under examination. To explain, the concentration of colorant in a particular cell exposed to the colorant may be less in a first region (e.g., nuclear region) than it is in a second region (e.g., cytoplasm region). Consequently the OD of the second region of the cell (e.g. cytoplasm) will be greater than the OD of the first region (e.g., nuclear) of the cell. In similar fashion, the fluorescent emissions from a particular region of a cell may be greater than the emissions from another region. Selectively using a portion of the fluorescent emission/OD values, which values represent greater emission intensity or OD, results in an improved noise to signal ratio that facilitates the analysis. This aspect takes advantage of the fact that colorants typically preferentially distribute, for example, within the granules within the cytoplasm of the cells.

Figure 9:
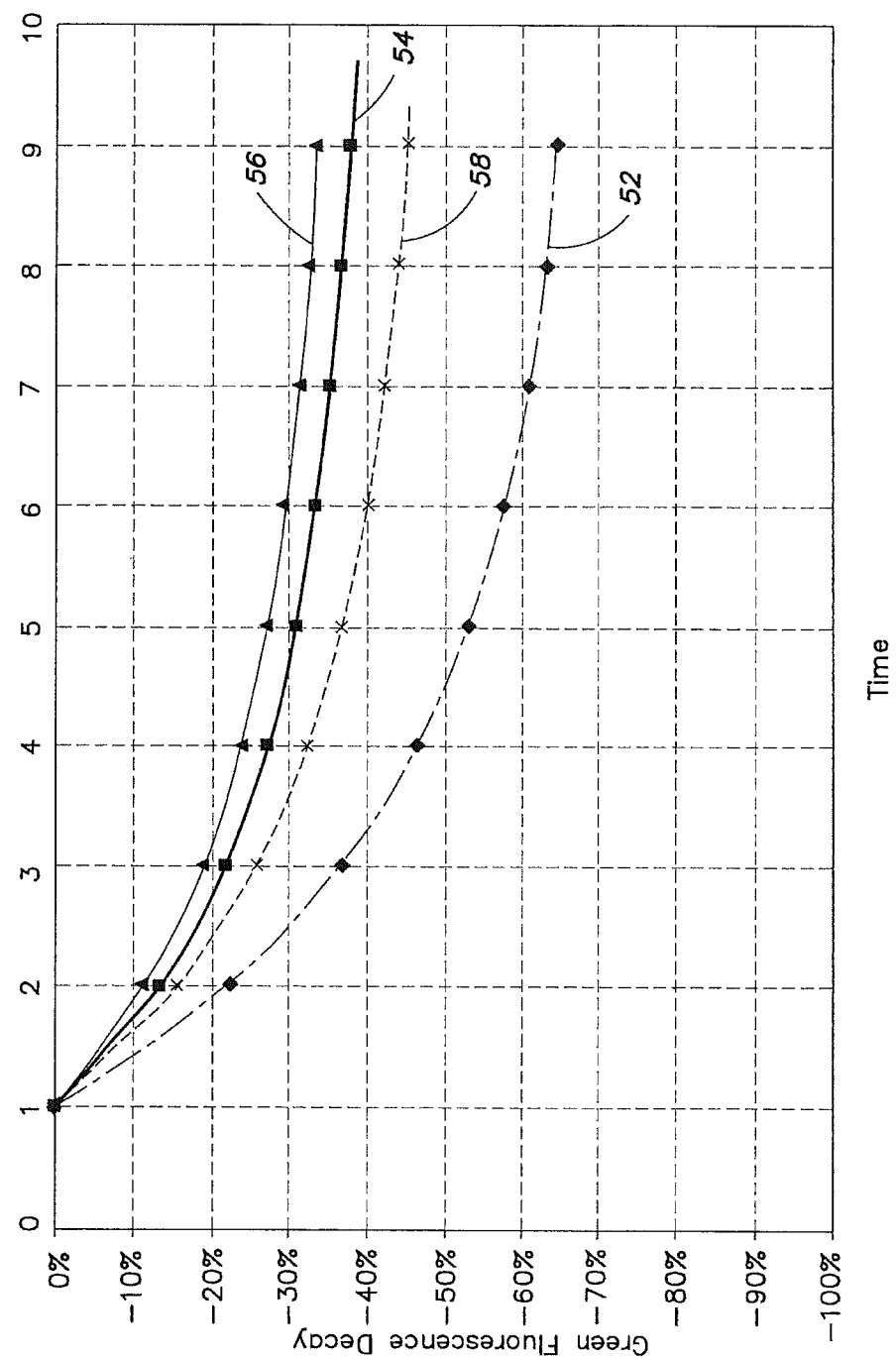
FIG. 9 is a graph diagrammatically illustrating an amount of fluorescent decay as a function of time for neutrophils.
Figure 10:
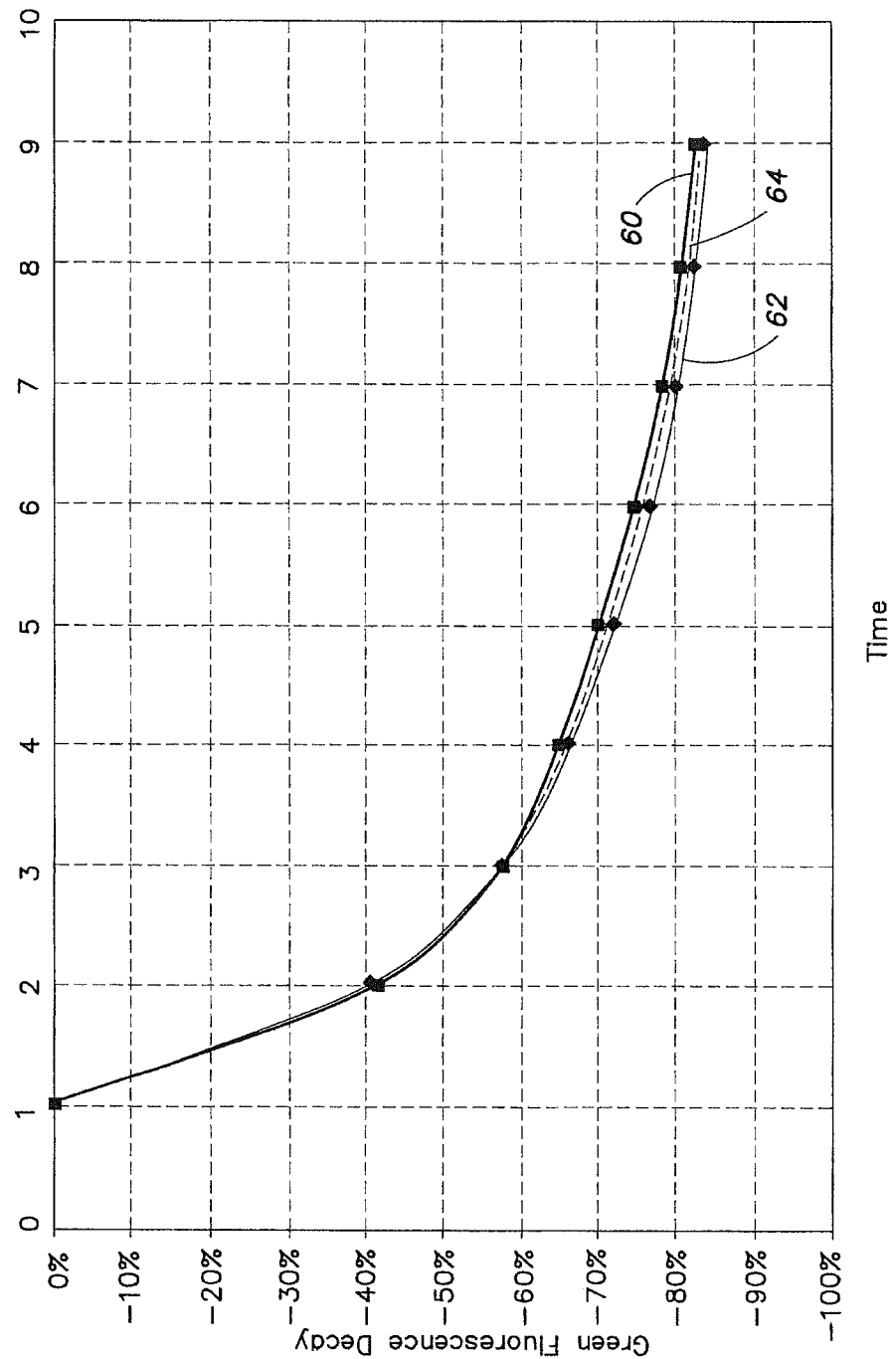
FIG. 10 is a graph diagrammatically illustrating an amount of fluorescent decay as a function of time for lymphocytes.

In a further embodiment of the present invention, the cells within the sample can be distinguished from one another by "bleaching" the cells admixed with the colorant with a constant emission of light at a wavelength (e.g., 470 nm) that excites a fluorescent emission, and sensing the magnitude of the emitted light at discrete points in time within a period of time. The average rate at which fluorescent emissions decrease in intensity from a particular cell type is constant for that cell type, but the average rates vary as between types of cells. Consequently, the decremental rate of intensity emission can be used to distinguish cell types. For example, FIG. 9 illustrates the rate of decay of green fluorescence emission for individual neutrophils exposed to photobleaching 52, 54, 56, and the average rate of decay for those neutrophils 58. FIG. 10 illustrates the rate of decay of green fluorescence emission for individual lymphocytes exposed to the same photobleaching 60, 62, and for the average 64 of those lymphocytes. The curves shown in FIGS. 9 and 10 clearly show different decay rates for the different cell types, and that the different rates of decay can be used to identify the type of cell being analyzed. The decremental rate of emission can also be used to distinguish cells by other characteristics such as age; e.g., cells of a certain type but different in age will have characteristic decremental rates of emission that can be used to distinguish the various different age groups.

Although this invention has been shown and described with respect to the detailed embodiments thereof, it will be understood by those skilled in the art that various changes in form and detail may be made without departing from the spirit and scope of the invention.

What is claimed is:

1. A method for analyzing at least one constituent of a biologic fluid sample quiescently residing within an analysis chamber defined by a first panel and a second panel, and which sample is mixed with at least one colorant that is operable to reside within the constituent and emit fluorescent light upon exposure to predetermined first wavelengths of light, the method comprising the steps of:
    illuminating at least a portion of the sample containing the constituent at one or more first wavelengths in a constant manner for a period of time;
    imaging the at least a portion of the sample at discrete points in time during the period, including producing image signals at the discrete points in time, which signals are indicative of fluorescent emissions from colorant residing within the constituent;
    determining one or more fluorescent emission values associated with the colorant residing within constituent using the image signals from the discrete points in time, and a rate of change for the fluorescent emission values between a plurality of the discrete points in time; and
    analyzing the constituent using the determined rate of change of the fluorescent emission values for the constituent.

2. The method of claim 1, wherein the analyzing step includes determining a characteristic of the constituent.

3. The method of claim 2, wherein the characteristic is an age of the constituent.

4. The method of claim 1, wherein the at least one constituent includes a first constituent and a second constituent;
    wherein the step of determining one or more fluorescent emission values includes determining the one or more fluorescent emission values from the colorant residing within the first constituent and from the second constituent using the image signals from the discrete points in time, and a rate of change for the fluorescent emission values between a plurality of the discrete points in time for each of the first constituent and the second constituent; and
    analyzing the first constituent and the second constituent using the determined rate of change of the fluorescent emission values for the respective constituent.

5. The method of claim 4, wherein the first constituent and the second constituent are a same type of constituent.

6. The method of claim 5, wherein the analyzing step includes determining a characteristic of the first constituent and the second constituent.

7. The method of claim 6, wherein the characteristic is an age of the respective constituent.

8. The method of claim 4, wherein the biologic fluid sample is substantially undiluted whole blood.

9. The method of claim 8, wherein the first and second constituents are selected from the group consisting of white blood cells and particulates.

10. The method of claim 9, wherein the first and second constituents are each types of white blood cells.

11. The method of claim 10, wherein the first constituents and the second constituents are selected from the group consisting of eosinophils, neutrophils, and basophils.

12. The method of claim 9, wherein the first and second constituents are each types of particulates.

13. The method of claim 12, wherein the first and second particulates are selected from a group consisting of platelets and hematoparasites.

14. The method of claim 1, wherein the one or more one or more values representative of fluorescent emission from the constituent are determined on a per pixel basis.

15. The method of claim 1, wherein the steps of determining one or more fluorescent emission values and analyzing the constituent are performed using one or more processors adapted to process the image signals.

16. The method of claim 1, wherein the step of determining one or more fluorescent emission values associated with the colorant includes determining fluorescent emission values at different wavelengths.

17. An apparatus for analyzing a blood sample, comprising:
  a chamber adapted to quiescently hold the sample;
  an illuminator operable to illuminate at least a portion of the sample containing a constituent, along one or more fluorescent excitation wavelengths in a constant manner for a period of time;
  an image dissector operable to image the at least a portion of the sample at discrete points in time during the period, and produce image signals representative of fluorescent emissions from the constituent at the discrete points in time; and
  an analysis device adapted to determine one or more fluorescent emission values for the constituent quiescently disposed within the sample using the image signals at the discrete points in time, and a rate of change for the fluorescent emission values between the discrete points in time, and adapted analyze the constituent using the determined rate of change of the fluorescent emission values for the constituent.

18. The apparatus of claim 17, wherein the constituent is selected from the group consisting of white blood cells and particulates.

19. The apparatus of claim 17, wherein the analysis device is operable to determine a characteristic of the constituent, using the image signals at the discrete points in time, and the rate of change for the fluorescent emission values between the discrete points in time.

20. The apparatus of claim 19, wherein the characteristic is an age of the constituent.

* * * * *

UNITED STATES PATENT AND TRADEMARK OFFICE
CERTIFICATE OF CORRECTION

| | | |
|---|---|---|
| PATENT NO. | : 8,502,963 B2 | |
| APPLICATION NO. | : 13/645075 | |
| DATED | : August 6, 2013 | |
| INVENTOR(S) | : Robert A. Levine et al. | |

It is certified that error appears in the above-identified patent and that said Letters Patent is hereby corrected as shown below:

In the Specification

Column 5, line 32, please delete "12, 15" and insert --12, 16--.

Signed and Sealed this
Seventeenth Day of September, 2013

Teresa Stanek Rea
*Deputy Director of the United States Patent and Trademark Office*